(12) United States Patent
Sexton

(10) Patent No.: US 8,770,210 B1
(45) Date of Patent: Jul. 8, 2014

(54) TRAVEL MOUTH CLEANING DEVICE

(71) Applicant: John Eric Sexton, Boynton Beach, FL (US)

(72) Inventor: John Eric Sexton, Boynton Beach, FL (US)

(73) Assignee: John E. Sexton, Boynton Beach, FL (US)

( * ) Notice: Subject to any disclaimer, the term of this patent is extended or adjusted under 35 U.S.C. 154(b) by 0 days.

(21) Appl. No.: 13/722,454

(22) Filed: Dec. 20, 2012

(51) Int. Cl.
*A45D 44/18* (2006.01)
*A61C 15/00* (2006.01)
*A46B 15/00* (2006.01)

(52) U.S. Cl.
CPC .................................. *A46B 15/0071* (2013.01)
USPC .......................................... 132/309; 132/329

(58) Field of Classification Search
USPC ......... 132/321, 323, 324, 325, 328, 329, 139, 132/146, 148, 149
See application file for complete search history.

(56) References Cited

U.S. PATENT DOCUMENTS

| | | | | |
|---|---|---|---|---|
| 5,419,346 A * | 5/1995 | Tipp | ............................... | 132/329 |
| 5,678,580 A * | 10/1997 | Sherman | ....................... | 132/324 |
| 2005/0155618 A1* | 7/2005 | Lafferty | ........................ | 132/104 |
| 2010/0107417 A1* | 5/2010 | Crisp | .............................. | 30/122 |

* cited by examiner

*Primary Examiner* — Rachel Steitz
(74) *Attorney, Agent, or Firm* — John E. Sexton

(57) ABSTRACT

A travel mouth-cleaning device contains a roll of floss, a plurality of teeth, a pick and a brush. The device may be used in a travel or non-travel capacity. The invention may be placed on a keychain that can be carried in the pants pocket or in a purse or other carrying container. The invention is small enough that it will not protrude the container while being transported. The invention can clean the tongue faster and easier than most conventional tongue scraper devices currently on the market, with a scraping action on the surface of the tongue from the plurality of teeth on the device. Moreover, all the necessary tools to clean the whole mouth are included within the device. Furthermore, the invention is easily transported so a person can clean their mouth after each meal while away from a place like their home bathroom or other facility. Moreover, to facilitate transportation the invention may be constructed of a material like a plastic polymer. Furthermore, the invention can be used in capacities like in the military in a pack called a MRE, (Meal Ready to Eat), while camping, or while traveling.

9 Claims, 3 Drawing Sheets

TRAVEL MOUTH CLEANING DEVICE

FIELD

This invention relates to consumer hygienic products and, more particularly, to an apparatus and a method for cleaning the mouth which can be used in a travel capacity or non-travel capacity.

BACKGROUND

Historically, mouth-cleaning devices have typically been individually divided separately into toothbrushes, tongue scrapers, floss, and picks. These individual devices have to be carried together separately while traveling. In regards to cleaning the tongue, one of the most unsanitary parts of the body, one must use a tongue cleaner. This tongue cleaner has historically been formed to be the size of a standard toothbrush, wherein an end portion having a scraper is connected to a long handle portion for manipulating the scraper. Additionally, this conventional tongue-cleaning device contains a scraper that may include abrasive surfaces, rubber fingers, plastic ribs, or other similar cleaning items having various shapes and forms intended to clean the surface portion of a tongue. Other previous embodiments include a U-shaped plate or other flat plate scrapers securely connected to a handle. All of these embodiments contain a scraper surface that is perpendicular to the longitudinal line of the handle of the device, thus causing the device to be awkward and cumbersome for travel. Moreover, in all instances the tongue-cleaning devices are bulky, not easily transported, and may take a long time to clean the surface of the tongue. The conventional construction is bulky and usually the size of a standard toothbrush. Furthermore, carrying a separate toothbrush, tongue scraper, floss, and pick can be cumbersome and not convenient. This would take up a lot of space in a woman's purse or man's pocket, for travel. Thus, when a person is on the go or traveling it is difficult to have all the necessary equipment to clean the mouth.

SUMMARY

An apparatus and method are provided for cleaning the mouth using a simple compact device. The invention is small and easily transported. To clean the tongue, a linear arrangement of a plurality of teeth on the device is placed perpendicular to the longitudinal line of the tongue, and a scraping movement removes the scum, foreign and odorous matter from the surface of the tongue. Moreover, to clean the crevices between the human teeth, the device contains a roll of floss that can expel floss for use and a tip for removing food or other particles from the gaps between the human teeth. Furthermore, a brush is attached to the tip of the device and can be used to brush and thus clean the human teeth.

In reference to the tongue cleaning scraper portion of the invention, a generally course natured plurality of teeth on the device are positioned and placed along the tongue and scraped from the back to the front of the tongue to remove course foreign matter from the tongue's surface. The invention then rotates, positions and places a generally fine natured plurality of teeth on the tongue to remove other, finer, foreign matter not removed with the generally course natured teeth, by scraping from the back to the front of the tongue. To clean between the human teeth, floss or a pick may be used. Additionally, to clean the human teeth a brush may be used. The fine and course natured teeth of the device, pick and brush are then cleaned by inserting the elongated body that contains the teeth, pick and brush repeatedly into a shroud that contains a plurality of bristles connected to the inside of the shroud. The inserting action and the bristles remove the scum and foreign matter attached to the device.

The ergonomics of the invention allows the device to be easily carried and thus used in a travel capacity. The ergonomic handle is parallel to the plurality of teeth attached to the elongated body and therefore has a sleek and slim contour, which will not become cumbersome or awkward for traveling. The generally course and fine natured teeth are arranged in a pattern wherein an individual tooth is juxtaposed next to another individual tooth in a linear fashion. Moreover, in one embodiment the device may be placed on a keychain disguised to look almost like a normal key via a hole placed in the handle. In another embodiment the invention can be used in the home or other capacity wherein it is not on a keychain. A shroud protects the integrity of the elongated body which contains a plurality of teeth along with a tip and brush. The shroud contains a plurality of bristles that clean the plurality of teeth, the tip and brush prior to storage or transport. To facilitate transport, the device may be constructed of a plastic polymer material or other robust material. Furthermore, features and advantages of the travel mouth cleaner in accordance with the present invention will be more fully apparent from the following detailed description and annexed drawings.

BRIEF DESCRIPTION OF THE DRAWINGS

The foregoing summary and the following detailed description of the embodiments are better understood when read in conjunction with the appended drawings. For the purposes of illustration, the subject matter is not limited to the specific methods and instrumentalities disclosed. In the drawings.

DETAILED DESCRIPTION

The subject matter of the described embodiments is described with specificity to meet statutory requirements. However, the description itself is not intended to limit the scope of this patent.

Figure 1:
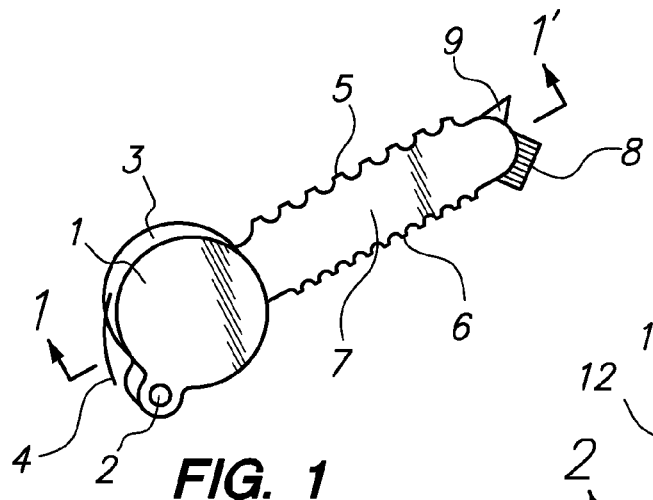
FIG. 1 is a perspective view of a roll of floss inside an ergonomic handle attached to an elongated body connected to a plurality of teeth, a brush and a tip.
Figure 2:
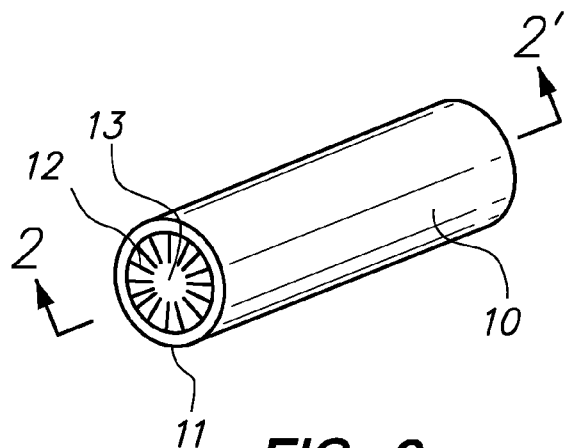
FIG. 2 is a perspective view of a shroud.
Figure 3:
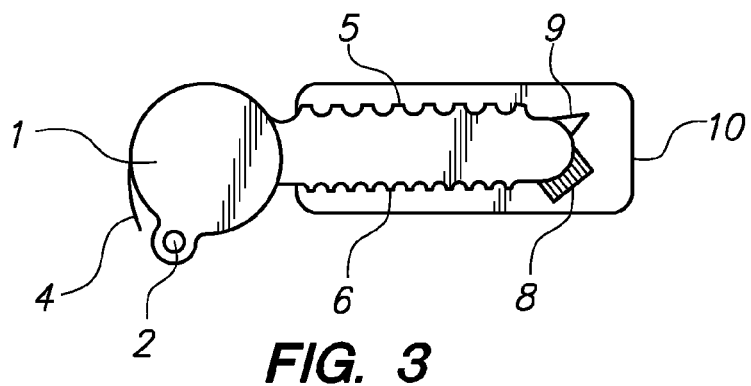
FIG. 3 is a cross sectional inside-view of an ergonomic handle attached to an elongated body connected to a plurality of teeth, a brush and a tip inserted into a shroud along the line 1-1' of FIG. 1.

Referring to FIG. 1, a perspective view of the basic structure and inter-relationship of the invention is shown. An ergonomic handle 1 connects to an elongated body 7. The ergonomic handle 1 contains a roll of floss 4. The ergonomic handle 1 contains a hole 2, wherein the hole 2 may attach to a standard keychain or other device. The elongated body 7 and ergonomic handle 1 contains a thickness 3 of or about 5 millimeters. Along a top of the elongated body 7 are attached a plurality of course natured teeth 5. Along a bottom of the elongated body 7 are attached a plurality of fine natured teeth 6. The generally course and fine natured teeth, 5 and 6, respectfully, are arranged in a pattern wherein an individual tooth is juxtaposed next to another individual tooth in a linear fashion. The ergonomic handle 1 is attached to the elongated body 7 in a parallel fashion, wherein the ergonomic handle 1 is not perpendicular to the lineage surface structure of the course natured teeth 5 and fine natured teeth 6. A brush 8 and a pick 9 are attached to the elongated body 7 opposite the ergonomic handle 1. Referring to FIGS. 1, 2 and 3, the elongated body 7 rests inside a shroud 10 for transport or storage as seen in FIG. 3. The shroud 10 has a thickness 11 of or about 3 millimeters. The shroud 10 contains a void 13 wherein the elongated body 7 fits. The invention has a length of or about 5 centimeters and a width of or about 2 centimeters.

Referring to FIG. 3, a cross sectional inside-view of the invention is described along the line 1-1' of FIG. 1 and along the line 2-2' of FIG. 2. An ergonomic handle 1 is connected to an elongated body 7. A plurality of teeth of a generally course nature 5 is connected to the top of the elongated body 7. A plurality of teeth of a generally fine nature 6 is connected to the bottom of the elongated body 7. The generally course and fine natured teeth, 5 and 6, respectfully, are arranged in a pattern wherein an individual tooth is juxtaposed next to another individual tooth in a linear fashion. A brush 8 and a pick 9 are attached to the elongated body 7 opposite the ergonomic handle 1. A shroud 10 protects the plurality of generally course and fine course natured teeth, 5 and 6, respectfully, the pick 9 and the brush 8.

Figure 4:
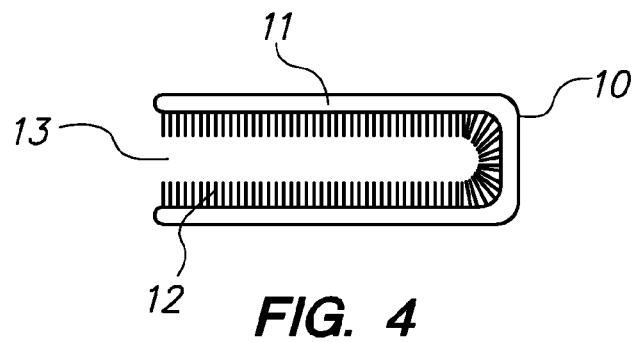
FIG. 4 is a cross sectional inside-view of a shroud with a plurality of bristles connected to the inside of the shroud, along the line 2-2' of FIG. 2.

Referring to FIG. 4, a cross sectional view taken along line 2-2' of FIG. 2 is described. A shroud 10 contains a thickness 10 of or about 3 millimeters. The shroud 10 contains a void 13 wherein an elongated body 7 as shown in FIGS. 1 and 3 fits inside securely. A plurality of generally course natured teeth 5 and generally fine natured teeth 6, pick 9, and brush 8 connected to the elongated body 7 as seen in FIGS. 1 and 3 are cleaned by inserting repeatedly into the shroud 10 wherein the plurality of bristles 12 remove the foreign matter attached to the device. Afterwards, the shroud 10 is placed around the elongated body 7 that contains the generally course and fine natured teeth, 5 and 6, respectfully, brush 8 and pick 9, as shown in FIG. 3, for transport or storage.

Figure 5:
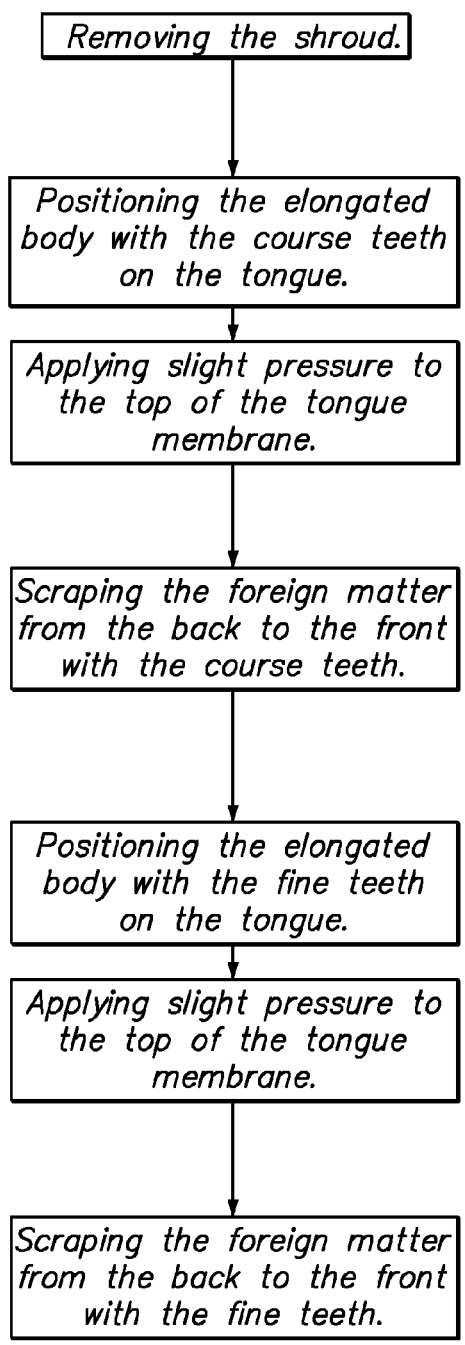
FIG. 5 is a flow diagram illustrating a method for cleaning a mouth.
Figure 5:
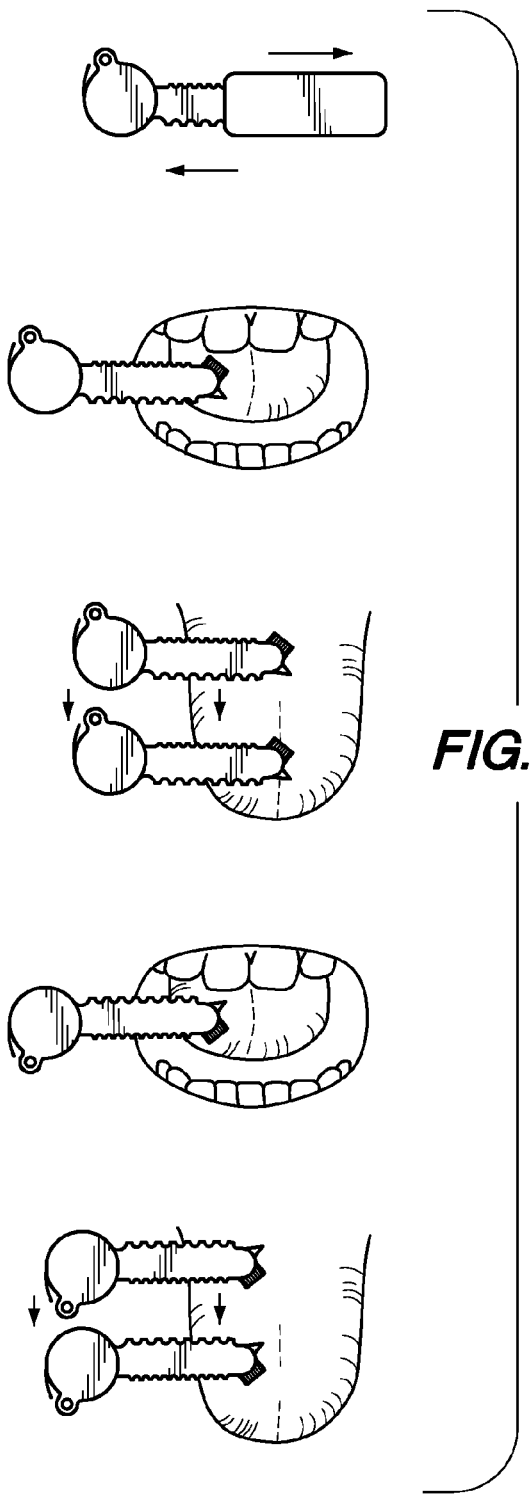
Figure 5:
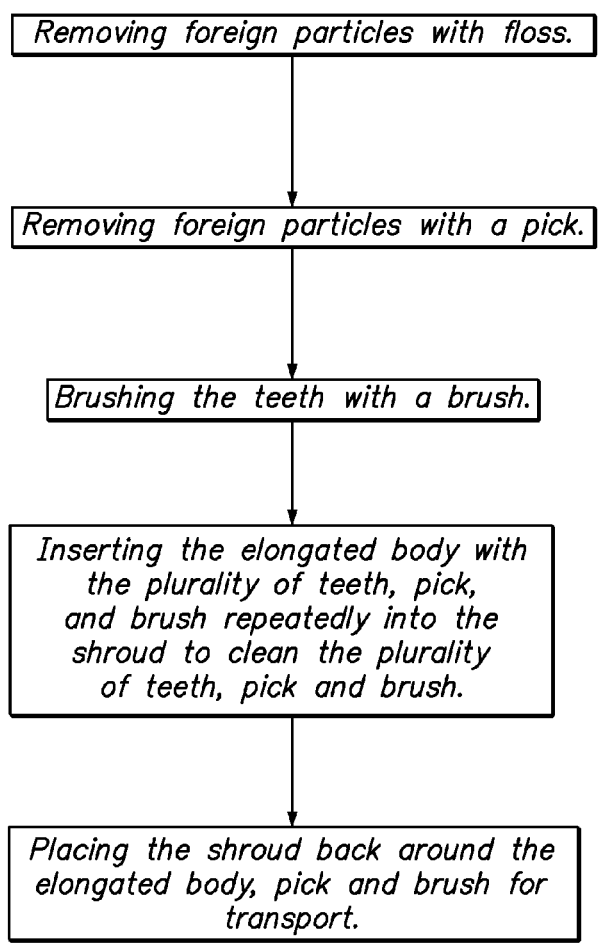
Figure 5:
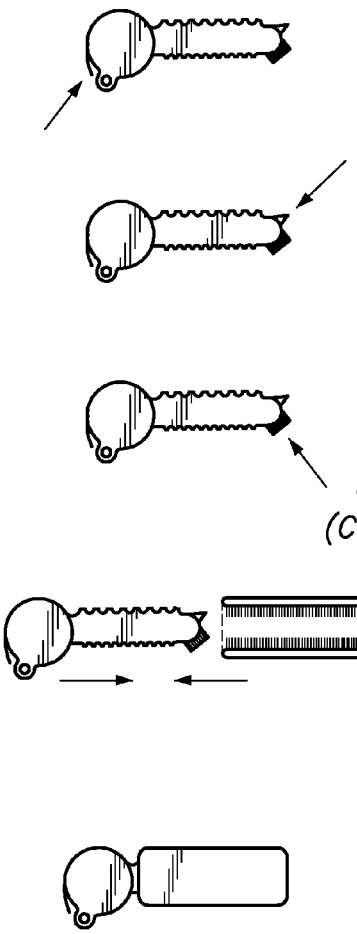

Referring to FIG. 5, a method for cleaning the tongue is described. Firstly, a shroud 10 is removed and an elongated body 7 containing a plurality of generally course natured teeth 5, a plurality of generally fine natured teeth 6, a pick 9, and a brush 8 are exposed. Next, the generally course natured teeth 5 are positioned perpendicular to the longitudinal nature of the tongue and pressed into the membrane of the tongue. The generally course natured teeth 5 scrape along the top of the membrane of the tongue from the back to the front repeatedly to remove foreign matter. Next, the generally fine natured teeth 6 are positioned perpendicular to the longitudinal nature of the tongue and pressed into the membrane of the tongue. The generally fine natured teeth 6 scrape along the top of the membrane of the tongue from the back to the front repeatedly, thereby removing foreign particles not removed with the generally course natured teeth 5. A roll of floss 4 expels floss from an ergonomic handle 1 to clean foreign matter between the human teeth. Next, the pick 9 is used to clean foreign matter between the human teeth. Next, the brush 8 is used to clean the human teeth. Next, the device is inserted into the shroud 10 containing a plurality of bristles 12 repeatedly to remove the foreign matter attached to the generally course and fine natured teeth, 5 and 6, respectfully, the pick 9, and the brush 8. Lastly, the elongated body 7, containing the generally course and fine natured teeth, 5 and 6, respectfully, the pick 9, and the brush 8, are inserted into the shroud 10, thereby into a void 13, for transport or storage.

What is claimed is:

1. A travel mouth cleaning device, comprising:
    a flat ergonomic handle;
    an elongated body connected to the handle;
    a roll of floss contained inside the handle;
    a pick connected to the elongated body;
    a brush connected to the elongated body;
    a plurality of teeth connected and orientated along a top and a bottom of the elongated body; and
    a shroud that surrounds the elongated body, the plurality of teeth, the pick and the brush, the shroud comprising a plurality of bristles connected and extended from the inside of the shroud.

2. The travel mouth cleaning device according to claim 1, wherein the plurality of teeth along the top of the elongated body comprises a generally course nature.

3. The travel mouth cleaning device according to claim 1, wherein the plurality of the teeth along the bottom of the elongated body comprises of a generally fine nature.

4. The travel mouth cleaning device according to claim 1, wherein the handle comprises a hole.

5. The travel mouth cleaning device according to claim 1, wherein the plurality of teeth comprises an arrangement in a pattern.

6. The travel mouth cleaning device according to claim 1, wherein the handle is parallel to the elongated body and the plurality of teeth.

7. The travel mouth cleaning device according to claim 1, wherein the pick connects to the elongated body, opposite wherein the handle connects to the elongated body.

8. The travel mouth cleaning device according to claim 1, wherein the brush connects to the elongated body, opposite wherein the handle connects to the elongated body.

9. A method for cleaning the mouth, comprising the steps of:
    Removing a shroud to expose an elongated body with a plurality of generally course and fine natured teeth, a pick and a brush;
    Positioning the elongated body with the plurality of course natured teeth in a perpendicular placement relative to a longitudinal nature of a tongue membrane;
    Applying slight pressure to the tongue membrane with the plurality of generally course natured teeth;
    Scraping and removing a foreign matter on the tongue membrane with the generally course natured teeth by moving from the back to the front of the tongue repeatedly;
    Positioning the elongated boy with the plurality of fine natured teeth in a perpendicular placement relative to the longitudinal nature of the tongue membrane;
    Applying slight pressure to the tongue membrane with the plurality of generally fine natured teeth;
    Scraping and removing a foreign matter on the tongue membrane with the generally fine natured teeth by moving from the back to the front of the tongue repeatedly;
    Removing foreign matter from between human teeth with a roll of floss that expels floss;
    Removing foreign matter from between the human teeth with the pick;
    Brushing the human teeth with the brush;
    Inserting the elongated body with the plurality of teeth, pick and brush into the shroud containing a plurality of bristles repeatedly, thereby removing and cleaning a foreign matter from the plurality of teeth, pick and brush; and
    Placing the shroud back around the elongated body, the plurality of teeth, pick, and brush for transport or storage.

* * * * *